United States Patent
Uslenghi et al.

(10) Patent No.: US 7,378,064 B2
(45) Date of Patent: May 27, 2008

(54) INDOOR AIR QUALITY MODULE WITH SAFETY SWITCHES TO DEACTIVATE ULTRAVIOLET LIGHT

(75) Inventors: Federico Uslenghi, Genoa (IT); Francesco Antonione, Milan (IT); Marco Occhetta, Milan (IT)

(73) Assignee: Carrier Corporation, Syracuse, NY (US)

( * ) Notice: Subject to any disclaimer, the term of this patent is extended or adjusted under 35 U.S.C. 154(b) by 533 days.

(21) Appl. No.: 10/789,962

(22) Filed: Feb. 27, 2004

(65) Prior Publication Data

US 2005/0189210 A1    Sep. 1, 2005

(51) Int. Cl.
*B01J 19/08* (2006.01)
(52) U.S. Cl. .................... 422/186.3; 422/121
(58) Field of Classification Search ............ 422/186.3, 422/121
See application file for complete search history.

(56) References Cited

U.S. PATENT DOCUMENTS

| | | | |
|---|---|---|---|
| 3,520,115 | A | 7/1970 | Bowen |
| 5,203,989 | A | 4/1993 | Reidy |
| 5,399,319 | A | 3/1995 | Schoenberger et al. |
| 6,797,042 | B2 | 9/2004 | LaFerriere et al. |
| 6,869,468 | B2 * | 3/2005 | Gibson ........................ 96/224 |
| 6,884,399 | B2 * | 4/2005 | Reisfeld et al. .......... 422/186.3 |

2005/0191219 A1    9/2005  Uslenghi et al.

FOREIGN PATENT DOCUMENTS

| | | |
|---|---|---|
| EP | 1281429 A1 | 2/2003 |
| EP | 1348488 A2 | 10/2003 |
| JP | 2000000433 | 1/2000 |
| JP | 2000-157621 A * | 6/2000 |

OTHER PUBLICATIONS

Supplementary European Search Report for Application No. 05712896.9—2213 PCT/US20050003619 mailed Oct. 26, 2007.

* cited by examiner

*Primary Examiner*—Kishor Mayekar
(74) *Attorney, Agent, or Firm*—Carlson, Gaskey & Olds

(57) ABSTRACT

An indoor air quality module includes an ultraviolet light source located between two titanium dioxide coated honeycombs. Photons of ultraviolet light are absorbed by the titanium dioxide coating to form reactive hydroxyl radicals that attack and oxidize contaminants in the to water, carbon dioxide, and other substances. An outer compartment is attached to an air duct and an HVAC unit, and an inner compartment supports the honeycombs, a particle filter, and the ultraviolet light source. When the module is in the working position and the honeycombs and the particle filter are correctly installed, the components contact switches on the outer compartment, and the ultraviolet light source is activated. When the inner compartment is pivoted relative to the outer compartment during servicing or if any of the components are incorrectly installed or not installed, one of the components does not engage the corresponding switch, deactivating the ultraviolet light source.

25 Claims, 4 Drawing Sheets

INDOOR AIR QUALITY MODULE WITH SAFETY SWITCHES TO DEACTIVATE ULTRAVIOLET LIGHT

BACKGROUND OF THE INVENTION

The present invention relates generally to an indoor air quality module that deactivates an ultraviolet light source if the module is being serviced or if the internal components are installed incorrectly or not installed.

Indoor air can include trace amounts of contaminants, including biospecies, dust, particles, odors, carbon monoxide, ozone, and volatile organic compounds (VOCs) such as formaldehyde, acetaldehyde, toluene, propanol, butene, etc. Indoor air quality modules are used to purify the air by destroying contaminants. The module includes a titanium dioxide coated monolith, such as a honeycomb, and an ultraviolet light source.

Titanium dioxide operates as a photocatalyst to destroy contaminants when illuminated with ultraviolet light. Photons of the ultraviolet light are absorbed by the titanium dioxide, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When contaminants in the air flow through the honeycomb and are adsorbed onto the titanium dioxide coating, the hydroxyl radicals attack and oxidize the contaminants to water, carbon dioxide, and other substances. The ultraviolet light also irradiates and kills the biospecies in the airflow.

If the honeycombs or an air filter are incorrectly installed or not installed in the module, ultraviolet light can leak from the module. Additionally, ultraviolet light can irradiate into the surrounding area during servicing of the module. Ultraviolet light may have several negative effects. For one, it may be harmful to the skin and to the eyes in high doses. Additionally, if ultraviolet light leaks from the module, less ultraviolet light is directed toward the titanium dioxide coating, reducing the number of hydroxyl radials and the photocatalytic effect of the titanium dioxide coating.

Hence, there is a need for an indoor air quality module that deactivates the ultraviolet light source if the module is being serviced or if the internal components are installed incorrectly or not installed.

SUMMARY OF THE INVENTION

An indoor air quality module (IAQ) purifies the air in an interior space. The module includes an ultraviolet light source located between two titanium dioxide coated honeycombs. When photons of ultraviolet light are absorbed by the titanium dioxide coating, reactive hydroxyl radicals are formed. When contaminants such as a volatile organic compounds or carbon monoxide flow through the honeycomb and adsorb onto the titanium dioxide coating, the hydroxyl radicals attack the contaminants. A hydrogen atom is abstracted from the contaminants, oxidizing the contaminants to water, carbon dioxide, and other substances. The module also decomposes ozone to oxygen and kills biospecies.

An inner compartment supports the honeycomb, the ultraviolet light source and an air filter. An outer compartment is attached to an air duct and a satellite indoor unit. A first end of the inner compartment is pivotally attached to the outer compartment, and the inner compartment is pivotal between a working position and a servicing position. An opposing second end of the inner compartment is removably attached to the outer compartment by fasteners.

When the module is in the working position and the honeycombs and the filter are correctly installed, each of the honeycombs and the particle filter contact a switch on the outer compartment. When all the components contact the corresponding switches, the ultraviolet light source is activated.

When the inner compartment is pivoted relative to the outer compartment and into the servicing position, the honeycombs and the particle filter disengage from the switches, and the ultraviolet light source is deactivated. The ultraviolet light source is also deactivated if the honeycombs or the particle filter are incorrectly installed or not installed in the inner compartment.

These and other features of the present invention will be best understood from the following specification and drawings.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
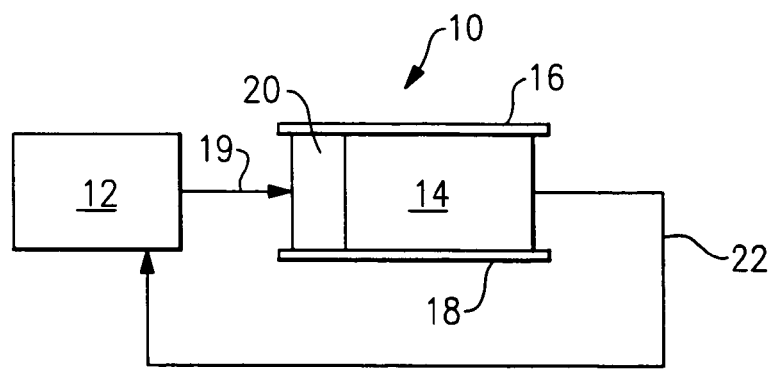
FIG. 1 schematically illustrates an enclosed environment, such as a building, vehicle or other structure, including an interior space and an HVAC system.

FIG. 1 schematically illustrates a structure 10, such as building or vehicle, that includes an interior space 12. The interior space 12 can be a room, an office or a vehicle cabin, such as a car, train, bus or aircraft. An HVAC system, such as a satellite indoor unit 14, heats or cools the interior space 12 of the structure 10. The satellite indoor unit 14 preferably is installed between a ceiling 16 and a false ceiling 18 in the structure 10. It should be understood that other arrangements will benefit from this invention.

Air in the interior space 12 is drawn into the satellite indoor unit 14 through an air duct 19. The satellite indoor unit 14 changes the temperature of the air drawn into the air duct 19. If the satellite indoor unit 14 is operating in a cooling mode, the air is cooled. Alternately, if the satellite indoor unit 14 is operating in a heating mode, the air is heated. The air is then returned to the interior space 12 through an air duct 22 to change the temperature of the air in the interior space 12.

An indoor air quality module 20 mounted between the air duct 19 and the satellite indoor unit 14 purifies the air before it is drawn into the satellite indoor unit 14. Alternately, the module 20 can purify the air leaving the satellite indoor unit 14 before returning into the interior space 12 or the module 20 can be a stand alone unit employed without the satellite indoor unit 14.

The indoor air quality module 20 oxidizes contaminants in the air, including volatile organic compounds, semi-volatile organic compounds and carbon monoxide, to water, carbon dioxide, and other substances. Examples of volatile organic compounds are aldehydes, ketones, alcohols, aromatics, alkenes, or alkanes. The indoor air quality module 20 also decomposes ozone to oxygen and kills biospecies.

Figure 2:
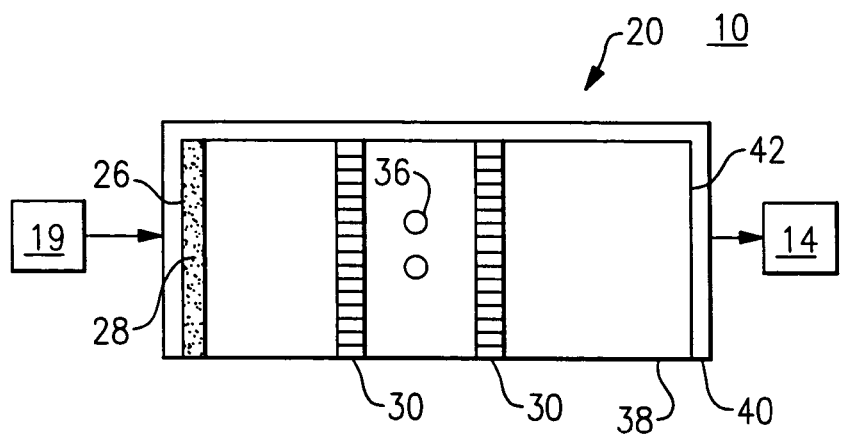
FIG. 2 schematically illustrates a side view of the indoor air quality module of the present invention.

FIG. 2 schematically illustrates a side view of the indoor air quality module 20 of the present invention. The indoor air quality module 20 defines a compartment. The air flows through a particle filter 28 that filters dust or other large particles from the air.

Figure 3:
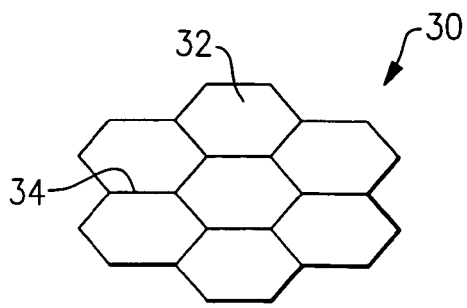
FIG. 3 schematically illustrates a front view of the honeycomb of the indoor air quality module.

The filtered air then flows through a monolith 30, such as a honeycomb 30 (FIG. 3). Preferably, there are at least two honeycombs 30 in the module 20 made of aluminum or an aluminum alloy. FIG. 3 schematically illustrates a front view of a portion of a honeycomb 30. The honeycomb 30 includes a plurality of hexagonal open passages 32 through which the air flows. The open passages 32 are coated with a photocatalytic coating 34, such as titanium dioxide. The titanium dioxide can also be doped or loaded with a metal oxide.

An ultraviolet light source 36 is positioned between the honeycombs 30. The ultraviolet light source 36 generates light having a wavelength in the range of 180 to 400 nanometers. If more than two honeycombs 30 are utilized in the module 20, the honeycombs 30 and the ultraviolet light source 36 alternate in the indoor air quality module 20. That is, an ultraviolet light source 36 is located between each of the honeycombs 30.

When illuminated by the ultraviolet light source 36, the titanium dioxide coating 34 on the honeycomb 30 is activated. Photons of ultraviolet light are absorbed by the titanium dioxide coating 34, promoting an electron from the valence band to the conduction band and producing a hole in the valence band. The electrons promoted to the conduction band are captured by oxygen. The holes in the valence band react with water molecules adsorbed on the titanium dioxide coating 34 to form reactive hydroxyl radicals.

When a volatile organic compound adsorbs onto the titanium dioxide coating 34, the hydroxyl radicals attack the volatile organic compound, abstracting a hydrogen atom from the volatile organic compound. The hydroxyl radicals oxidize the volatile organic compounds and produce water, carbon dioxide, and other substances. The purified air then exits the indoor air quality module 20 through an outlet 42.

As air flow through the module 20, the particle filter 28 acts as a mechanical filter to remove dust and particles. When illuminated by the ultraviolet light source 36, the titanium dioxide coated 34 honeycombs 30 oxidize and destroy volatile organic compounds. Finally, the ultraviolet light generated by the ultraviolet light source 36 has a germicidal effect to kill biospecies.

The indoor air quality module 20 further includes an outer compartment 40 and an inner compartment 38 that contains the particle filter 28, the honeycombs 30 and the ultraviolet light source 36. The inner compartment 40 is pivotally attached to the outer compartment 40 and pivotal between a working position and a servicing position. The outer compartment 40 is attached to the air duct 19 and to the satellite indoor unit 14 and houses the electric, electronic and safety related components. During operation of the module 20, the inner compartment 38 is contained in the outer compartment 40.

Figure 4:
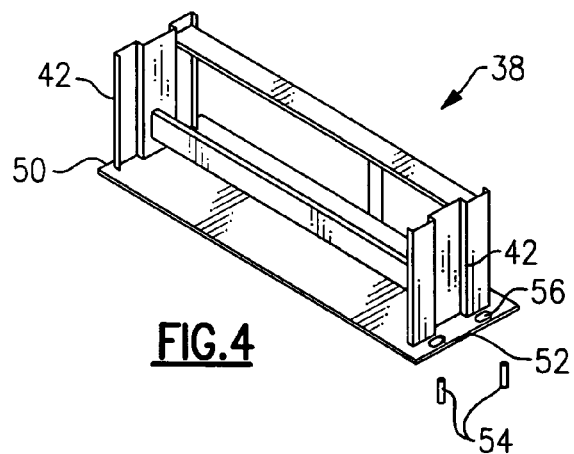
FIG. 4 schematically illustrates the inner compartment without any internal components.

FIG. 4 schematically illustrates the inner compartment 38 of the indoor air quality module 20 without the filter 28, the honeycombs 30, and the ultraviolet light source 32. The inner compartment 38 includes a first end 50 pivotally attached to the outer compartment 40, an opposing second end 52, and opposing side portions 42 that support the filter 28, the honeycomb 30 and the ultraviolet light source 32 and prevent these components from accidentally disengaging from the inner compartment 38. When installed in the inner compartment 38, the honeycombs 28 and the ultraviolet lights 24 are parallel. The pivotal attachment of the inner compartment 38 to the outer compartment 40 allows maintenance of the module 20 to be done by a single person.

The second end 52 of the inner compartment 38 is removably attached to the outer compartment 40 by fasteners 54, such as screws. In one example, two fasteners 54 are employed to secure the second end 52 to the outer compartment 40. By utilizing two fasteners 54, additional security is provided to maintain the inner compartment 38 within the outer compartment 40. Each fastener 54 is received in an aperture 56 in the inner compartment 38 that aligns with an aperture (not shown) in the outer compartment 40 to secure the inner compartment 38 inside the outer compartment 40.

Figure 5:
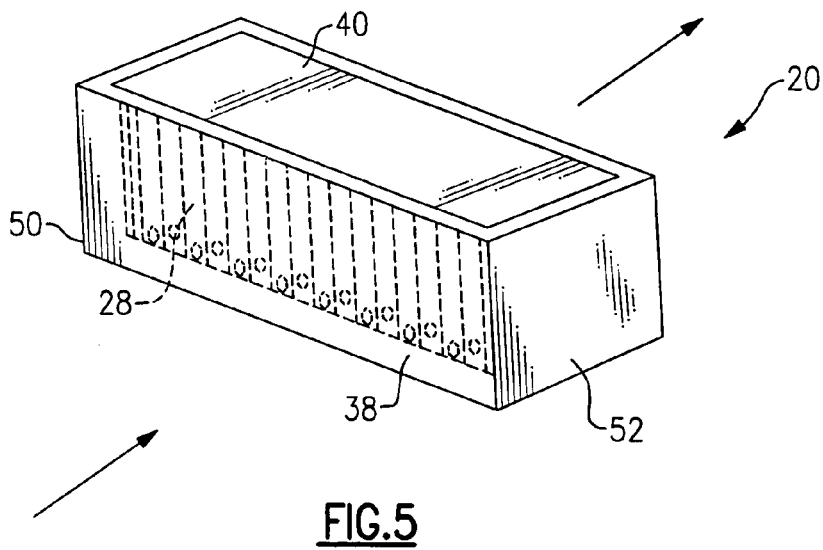
FIG. 5 schematically illustrates the indoor air quality module in the working position.
Figure 6:
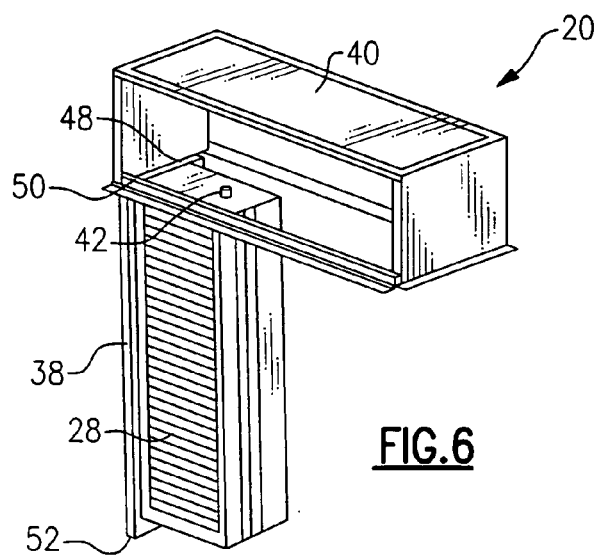
FIG. 6 schematically illustrates the indoor air quality module in the service position.

FIG. 5 schematically illustrates the indoor air quality module 20 in the working position when the inner compartment 38 is received in the outer compartment 40. When servicing is required, the fasteners 54 are removed from the second end 52 of the inner compartment 38. The inner compartment 38 is then pivoted relative to the outer compartment 40 about the first end 50 to the servicing position (FIG. 6). The operator can access the air filter 28, the honeycombs 30, and the ultraviolet light source 36 in the inner compartment 38. In the servicing position, the inner compartment 38 is substantially perpendicular to the outer compartment 40. Maintenance and service operations can be accomplished without removing the indoor air quality module 20, the air duct 19, or the indoor satellite unit 14. When in the servicing position, the side support portions 42 support the internal components and prevents the components from falling out of the inner compartment 38.

When servicing is complete, the inner compartment 38 is pivoted relative to the outer compartment 40 about the first end 50 and into the working position (FIG. 5). The fasteners 54 are reinserted into the aligned apertures 56 of the inner compartment 40 and the outer compartment 40 to secure the inner compartment 40 in the working position.

Figure 7:
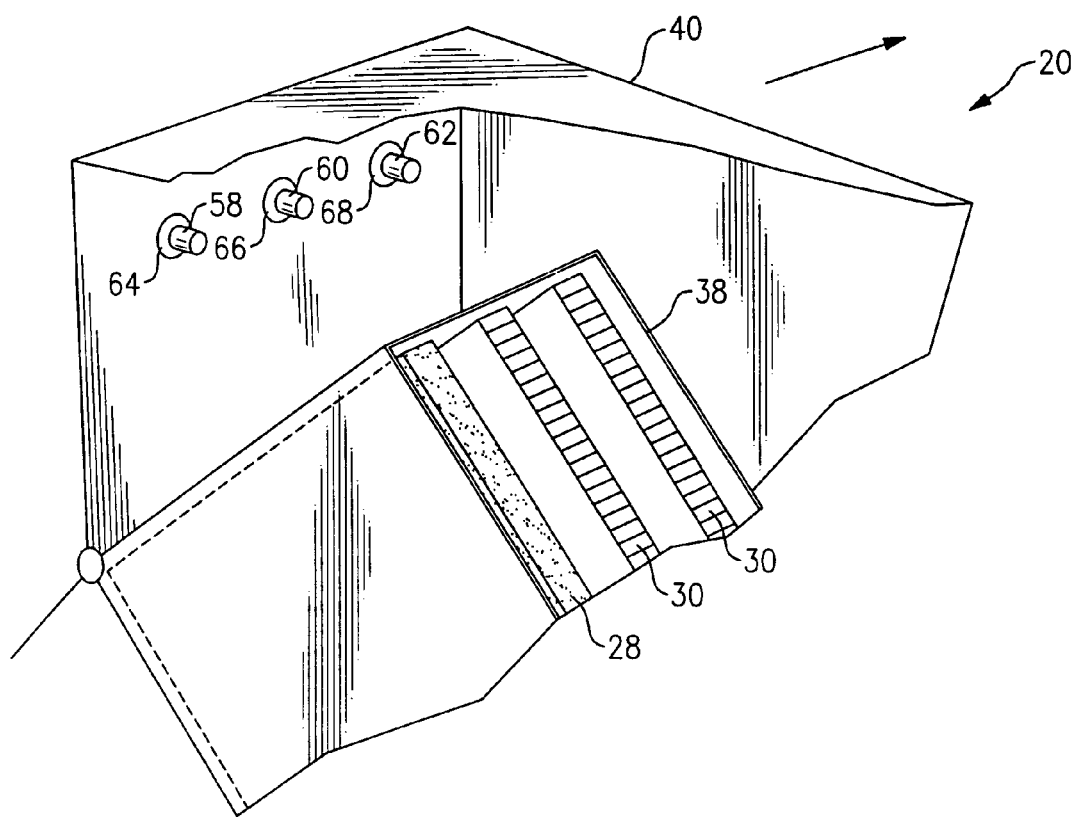
FIG. 7 schematically illustrates a perspective view of the indoor air quality module of the present invention.

FIG. 7 schematically illustrates a perspective view of the module 20 of the present invention. The module 20 includes switches 58, 60 and 62 that are located the outer compartment 40 and extend through a respective opening 64, 66 and 68 in the outer compartment 40. Switch 58 corresponds to the particle filter 28, switch 60 corresponds to one honeycomb 30, and switch 68 corresponds to the other honeycomb 30.

Figure 8:
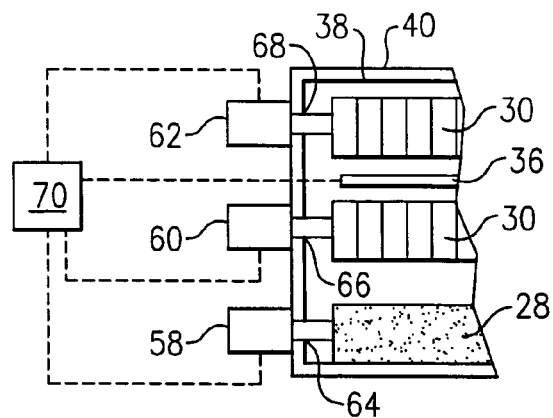
FIG. 8 schematically illustrates a top view of the indoor air quality module of the present invention including the switches.
Figure 9:
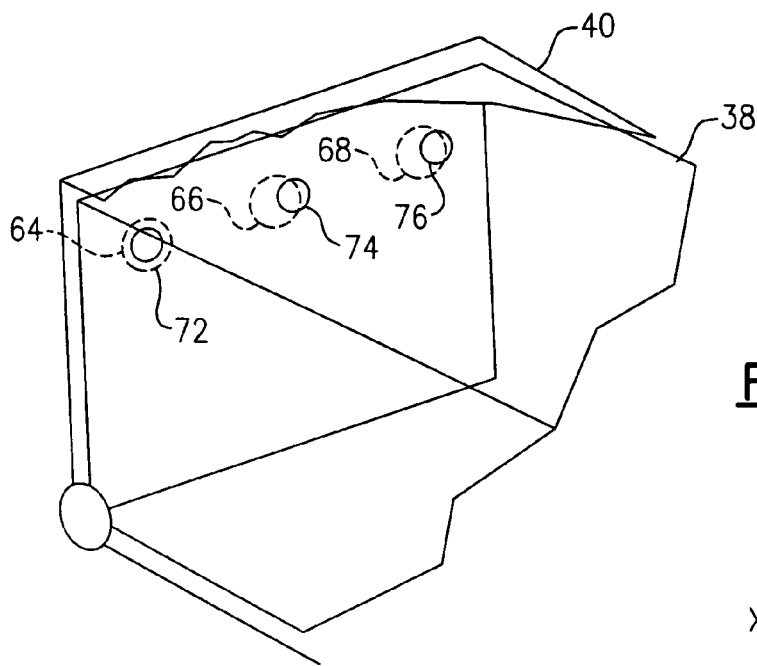
FIG. 9 schematically illustrates a perspective view of the apertures of the inner compartment and the outer compartment.

FIG. 8 schematically illustrates the module 20 in the working position. When the particle filter 28 and the honeycombs 30 are correctly installed, the particle filter 28 and the honeycombs 30 contact the corresponding switch 58, 60 and 62. When the switches 58, 60 and 62 are all engaged, the ultraviolet light source 36 is activated to generate ultraviolet light. The switches 58, 60 and 62 extend through a corresponding opening 72, 74 and 76 in the inner compartment 38 to contact the respective particle filter 28 and honeycomb 30 (FIG. 9).

A cable clamp 70 powers the ultraviolet light source 36. The switches 58, 60 and 62 are connected in series and located between the cable clamp 70 and the ultraviolet light source 36. If the particle filter 28 or the honeycombs 30 do not contact the corresponding switch 58, 60 and 62, the cable clamp 70 prevents the flow of power to the ultraviolet light source 36 to stop the generation of ultraviolet light.

When the inner compartment 38 is pivoted to the service position (FIG. 6), the particle filter 28 and the honeycombs 30 disengage from the respective switch 58, 60 and 62. As the switches 58, 60 and 62 do not detect the respective particle filter 28 or honeycombs 30, the cable clamp 70 deactivates the ultraviolet light source 36 and ultraviolet light is not generated. Therefore, when the inner compartment 38 is pivoted to the service position, the ultraviolet light source 36 does not generate ultraviolet light, preventing ultraviolet light from the escaping module 20 and into the surrounding area during servicing.

The ultraviolet light source 36 is also deactivated if the particle filter 28 or the honeycombs 30 are installed incorrectly or not installed. By deactivating the ultraviolet light source 36 when the components are not installed or incorrectly installed, leakage of ultraviolet light from the module 20 is prevented.

If any of the switches 58, 60 and 62 do not detect the respective particle filter 28 or honeycomb 30, the particle filter 28 or the honeycombs 30 may be installed incorrectly or may not be installed. The cable clamp 70 prevents power to the ultraviolet light source 36 to stop the generation of ultraviolet light. That is, if any of the switches 58, 60 and 62 do not detect the respective particle filter 28 or honeycomb 30, the ultraviolet light source 36 is deactivated.

Figure 10:
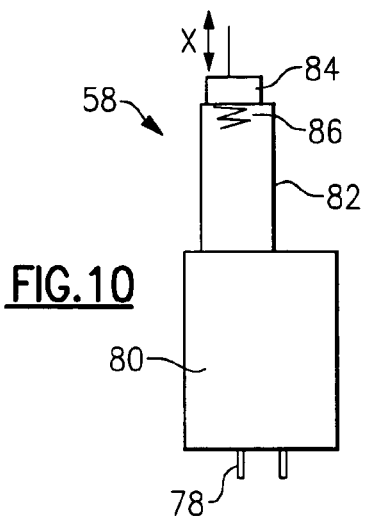
FIG. 10 schematically illustrates a switch of the present invention.

FIG. 10 schematically illustrates a switch 58 of the present invention. Although only the switch 58 is illustrated and described, it is to be understood that the switches 60 and 62 operate in a similar manner. The switch 58 includes a body portion 80 and an electrical connector 78 in communication with the cable clamp 70. A finger 82 of the switch 58 projects through the opening 64 of the outer component 40 and includes a sensing pad 84. A resilient member 86 allows the sensing pad 84 to move in the X direction. When the particle filter 28 is correctly installed and the module 20 is in the working position, the particle filter 28 contacts the sensing pad 84, and the sensing pad 84 senses the presence of the particle filter 28.

For example, if the particle filter 28 is not installed properly, the particle filter 28 does not engage the sensing pad 84, indicating the particle filter 28 is either incorrectly installed or not installed in the internal compartment 38. The ultraviolet light source 36 will not generate ultraviolet light, preventing the leakage of ultraviolet light from the module 20. Although the contact of the particle filter 28 and the switch 58 is described, it is to be understood that the contact of the honeycombs 30 and the switches 60 and 62 operate in a similar manner. That is, if either of the switches 60 and 62 do not contact the respective honeycomb 30, the ultraviolet light source 36 will not generate ultraviolet light.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. An indoor air quality module comprising:
    an outer compartment attachable to a component, and the outer compartment includes a switch;
    an inner compartment pivotally attached to the outer compartment and having an inlet, an outlet, an ultraviolet light source, and a filtering device located between the inlet and the outlet; and
    a controller for the ultraviolet light source, and the controller is configured to activate the ultraviolet light source when the switch detects the filtering device.

2. The module as recited in claim 1 wherein the filter device is a monolith, and a photocatalytic coating is applied on the monolith, and the ultraviolet light source is configured to activate the photocatalytic coating.

3. The module as recited in claim 2 wherein the monolith defines a first monolith, a second monolith, and the ultraviolet light source is located between the first monolith and the second monolith, and the switch comprises a first switch and a second switch, and the controller is configured to activate the ultraviolet light source when the first switch detects the first monolith and the second switch detects the second monolith.

4. The module as recited in claim 1 wherein the filter device is a particle filter, and the controller is configured to activate the ultraviolet light source when the switch detects the particle filter.

5. The module as recited in claim 1 wherein the inner compartment includes a first end and an opposing second end, and the first end is pivot ally attached to the outer compartment and pivotal between a first position and a second position.

6. The module as recited in claim 5 wherein the switch is proximate to the first end of the inner compartment.

7. The module as recited in claim 6 wherein the filter device disengages from the switch when the inner compartment is in the second position, and the controller deactivates the ultraviolet light source.

8. The module as recited in claim 7 wherein the inner compartment is substantially parallel to the outer compartment in the first position and the inner compartment is substantially perpendicular to the outer compartment in the second position.

9. The module as recited in claim 1 wherein the switch does not engage the filter device when the filter device is incorrectly installed.

10. The module as recited in claim 1 wherein the photocatalytic coating is titanium dioxide.

11. The module as recited in claim 1 wherein the monolith is a honeycomb having a plurality of hexagonal shaped passages.

12. The module as recited in claim 1 wherein the inner compartment houses a particle filter.

13. The module as recited in claim 1, wherein the switch includes a body portion, an electrical connector configured to communicate with a cable clamp, and a finger having a sensing pad, the sensing pad configured to detect the filtering device in response to the filtering device contacting the sensing pad.

14. The module as recited in claim 1 wherein the inner compartment is pivotal between an open position and a closed position, and the switch detects the filtering device in response to the inner compartment being positioned at the closed position.

15. An indoor air quality module comprising:
an outer compartment. attachable to a component, and the outer compartment includes a first monolith switch, a second monolith switch, and a filter switch;
an inner compartment pivotally attached to the outer compartment and having an inlet, an outlet, a first monolith located between the inlet and the outlet having a photocatalytic coating, a second monolith located between the inlet and the outlet having the photocatalytic coating, a particle filter, and an ultraviolet light source located between the first monolith and the second monolith to activate the photocatalytic coating; and
a controller for the ultraviolet light source, and the controller is configured to activate the ultraviolet light source when the first monolith detects the first monolith, the second monolith switch detects the second monolith and filter switch detects the particle filter.

16. The module as recited in claim 15 wherein the inner compartment includes a first end and an opposing second end, and the first end of the inner compartment is pivotally attached to the outer compartment and is pivotal between a first position and a second position.

17. The module as recited in claim 16 wherein the first monolith switch disengages from the first monolith, the second monolith switch disengages from the second monolith and the filter switch disengages from the particle filter when the inner compartment is in the second position, and the controller deactivates the ultraviolet light source.

18. The module as recited in claim 15 wherein each of the first monolith switch, the second monolith switch and the filter switch include a body portion, an electrical connector configured to communicate with a cable clamp, and a finger having a sensing pad, and each of the sensing pads configured to detect one of the first monolith, the second monolith and the particle filter in response to each of the first monolith, the second monolith and the particle filter contacting one of the sensing pads.

19. The module as recited in claim 15 wherein the inner compartment is pivotal between an open position and a closed position, and the first monolith switch detects the first monolith, the second monolith switch detects the second monolith and the filter switch detects the particle filter in response to the inner compartment being positioned at the closed position.

20. A method of purifying air comprising the steps of:
pivotally attaching a first end of an inner compartment to an outer compartment, the inner compartment including a filtering device;
flowing air through the filtering device;
sensing the filtering device;
illuminating an ultraviolet light source if the step of sensing detects the filtering device; and
deactivating the ultraviolet light source if the step of sensing does not detect the filtering device.

21. The method as recited in claim 20 wherein the filtering device is a monolith having a titanium dioxide coating, and the step of illuminating activates the titanium dioxide coating.

22. The method as recited in claim 20 wherein the filtering device is a particle filter.

23. The method as recited in claim 20, wherein the step of pivotally attaching the first end of the inner compartment includes pivoting the inner compartment between a first position and a second position.

24. The method as recited in claim 23, comprising the step of positioning a switch proximate to the first end of the inner compartment.

25. The method as recited in claim 24, comprising the step of disengaging the filtering device from the switch when the inner compartment is in the second position.

* * * * *

UNITED STATES PATENT AND TRADEMARK OFFICE
CERTIFICATE OF CORRECTION

PATENT NO. : 7,378,064 B2
APPLICATION NO. : 10/789962
DATED : May 27, 2008
INVENTOR(S) : Uslenghi et al.

Page 1 of 1

It is certified that error appears in the above-identified patent and that said Letters Patent is hereby corrected as shown below:

Claim 5, Column 6, line 37: "pivot ally" should read as --pivotally--

Signed and Sealed this

Fifth Day of August, 2008

JON W. DUDAS
*Director of the United States Patent and Trademark Office*